United States Patent [19]

Hirsch et al.

[11] Patent Number: 4,801,594
[45] Date of Patent: Jan. 31, 1989

[54] AROMATASE INHIBITORS

[75] Inventors: Kenneth S. Hirsch, New Palestine; Charles D. Jones, Indianapolis, both of Ind.

[73] Assignee: Eli Lilly and Company, Indianapolis, Ind.

[21] Appl. No.: 621,582

[22] Filed: Jun. 18, 1984

[51] Int. Cl.$^4$ ...................... A61K 31/41; A61K 31/44
[52] U.S. Cl. .................................... 514/340; 514/359; 514/381
[58] Field of Search ................ 424/269; 514/340, 359, 514/381

[56] References Cited

U.S. PATENT DOCUMENTS

| | | | |
|---|---|---|---|
| 4,094,881 | 6/1978 | Berges | 548/255 |
| 4,098,894 | 7/1978 | Buchal et al. | 514/359 |
| 4,227,004 | 10/1980 | Wildonger | 548/255 |

FOREIGN PATENT DOCUMENTS 1511195  5/1978  United Kingdom .

OTHER PUBLICATIONS

Chem. Abst., 71, 61296p (1969).
Chemical Abstracts 89:24368q (1978).
Fisher, et al., "5-Aroyltetrazoles," *J. Org. Chem.*, 24, 1650 (1959).
Burgess, et al., "Synthesis . . . of . . . Azafulvenes," *J. Org. Chem.*, 39(7), 940 (1974).
Adelstein, "Antiarrhythmic Agents . . . ", *J. Med. Chem.*, 16(4), 309 (1973).
Balieu, et al., "Tetrazole Analogues . . . ", *Acta Chemica Scandinavica*, 27, 1233 (1973).
Chemical Abstracts 89:179927v (1978).
Balieu, et al., "Tetrazole Analogues . . . ", *Acta Chemica Scandinavica*, 26, 2951 (1972).
Zaugg et al., "Reactions of some ester alkaloids . . . ," *J. Org. Chem.*, 23, 847 (1958).

*Primary Examiner*—Christopher Henderson
*Attorney, Agent, or Firm*—Robert A. Conrad; Leroy Whitaker

[57] ABSTRACT

This invention provides azole derivatives, their pharmaceutical formulations, and their use in methods of inhibiting aromatase and treating or preventing estrogen-dependent diseases in mammals.

15 Claims, No Drawings

AROMATASE INHIBITORS

BACKGROUND OF THE INVENTION

Estrogens are synthesized from androgenic steroids. In the biosynthetic pathway for estrogen formation, aromatization is an essential step. It is generally believed that if the aromatase enzyme could be effectively inhibited, a useful treatment for estrogen dependent disorders could be obtained (see *Cancer Research,* Vol. 42, Suppl. 8: 3261s (1982)).

Several estrogen dependent diseases exist which could be treated with aromatase inhibitors. These include breast cancer, endometriosis, polycystic ovarian disease, benign breast disease, and endometrial cancer. A beneficial effect of antiestrogens in the treatment of breast cancer has been well established (see *Br. J. Cancer,* 25, 270 (1971)). Two of the known aromatase inhibitors, testolactone and aminoglutethimide, have shown a beneficial effect in treatment of breast cancer. See *Cancer Research,* supra.

Endometriosis is characterized by an abnormal proliferation of the endometrium of the uterus. Since the endometrium is dependent on estradiol for its growth, an inhibitor of estrogen production should stop the progression of the disease.

Benign breast disease, or often called fibrocystic breast disease, appears to be dependent on ovarian steroids. See *Cancer,* 49, 2534 (1982). Aromatase inhibitors have not been tried in this disease, but antiestrogens seem to be of benefit. See *Obstet. Gynecol.,* 54, 80 (1979).

Polycystic ovarian disease is one of the most common causes of infertility in women. The disease appears to result from an abnormality in steroid metabolism, and the major form of therapy in this disease is the antiestrogen, clomiphene. See *Clin. Endocrinol.,* 12, 177 (1980).

It is the purpose of this invention to provide novel azole derivatives, their pharmaceutical formulations, and a method of inhibiting the enzyme aromatase in mammals employing the azole derivatives. The invention thus provides for the treatment or prevention of breast cancer and other estrogen-dependent diseases.

SUMMARY OF THE INVENTION

This invention provides triazole and tetrazole compounds of the formula

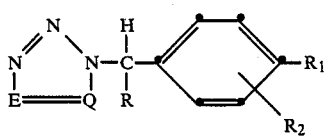

I wherein R is pyridyl or

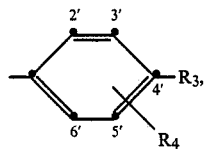

$R_1$, $R_2$, $R_3$, and $R_4$ are independently hydrogen, methyl, trifluoromethyl, methoxy, or halo; and E and Q are independently N or CH, with the proviso that E and Q may not both be N at the same time, or a pharmaceutically acceptable salt thereof.

In addition, this invention provides a method of inhibiting aromatase in mammals which comprises administering an aromatase inhibiting amount of a compound of the above formula. By virtue of their ability to inhibit the enzyme aromatase, the compounds of the above formula are useful in the treatment and prevention of estrogen-dependent diseases, espcially breast cancer, in mammals.

Further provided by this invention are pharmaceutical formulations comprising one or more of the compounds of the above formula in combination with a suitable pharmaceutical carrier, diluent, or excipient therefor. The formulations provided by this invention are particularly useful in treating mammals suffering from estrogen-dependent diseases such as breast cancer.

DETAILED DESCRIPTION AND PREFERRED EMBODIMENT

The term "halo" refers to fluoro, chloro, bromo, and iodo. "Pyridyl" refers to 2-, 4-, or especially 3-pyridyl.

A preferred group of compounds useful in this invention are those wherein:

(a) $R_1$ is halo, especially fluoro or chloro, or trifluoromethyl, and (b) R is phenyl ($R_3$ and $R_4$ are both hydrogen) or substituted phenyl, especially where $R_3$ is halo, especially chloro or fluoro, or trifluoromethyl.

Especially preferred compounds are those wherein (a) $R_1$ and $R_2$ are both chloro, especially 3,4-dichloro, and R is unsubstituted phenyl, or (b) is mono-substituted phenyl, $R_1$ and $R_3$ are independently chloro or fluoro, and $R_2$ and $R_4$ are each hydrogen.

The most preferred compounds provided by this invention are 1-[bis(4-chlorophenyl)methyl]-1H-1,2,3-triazole and 2-[bis(4-chlorophenyl)methyl]-2H-tetrazole, and pharmaceutically acceptable salts thereof.

As will be recognized by those skilled in the art, the compounds of the above formula may contain an asymmetric carbon atom. This invention is not limited to any particular isomer but includes the individual enantiomers as well as the racemates of the compounds.

In addition, when one of E and Q is N and the other is CH, the compounds of the above formula are 1- or 2-substituted tetrazoles. Although each of these two types of tetrazoles are claimed individually, because of the method of preparation, the two isomers may be formed together. Thus, this invention includes the individual 1- and 2-substituted tetrazoles and mixtures thereof. This latter mixture is referred to herein as 1(2)-substituted tetrazoles.

The pharmaceutically acceptable acid addition salts of the bases represented by the above formula can be prepared employing those acids of sufficient acidity to form acid addition salts. These include both inorganic and organic acids such as hydrochloric, hydrobromic, hydriodic, sulfuric, phosphoric, oxalic, methanesulfonic, benzenesulfonic, p-toluenesulfonic, maleic, and the like acids. Preferred acids for salt formation are the inorganic acids, especially hydrochloric acid.

The compounds of this invention may be prepared by any of several methods. The preferred method of preparing these compounds is summarized by the following scheme:

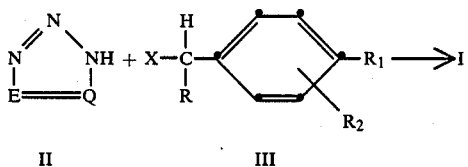

where X is halo, preferably chloro or bromo, or hydroxy. Generally, compounds II and III are allowed to react together in the presence of a base, such as an alkali metal hydride, hydroxide, alkoxide, or carbonate, preferably in the presence of a non-reactive high boiling solvent, such as dioxane, a dialkylformamide, such as dimethylformamide, and the like. Typically, an excess of the azole derivative II is employed, usually between a slight excess and a 6-fold molar excess. The reaction is generally carried out under an inert atmosphere and at temperatures from about 20° C. up to the boiling point of the reaction mixture. Under the preferred reaction conditions of sodium hydride and dimethylformamide at about 80°–100° C., the reaction is usually complete within about 2–24 hours. Intermediates II and III are either commercially available, are known in the literature, or can be prepared by methods known in the art.

In order to more fully illustrate the preperation of the compounds of this invention, the following examples are provided. The examples are illustrative only and are not intended to limit the scope of the invention in any way.

EXAMPLE 1

2-[Bis(4-chlorophenyl)methyl]-2H-tetrazole

A. Preparation of 4,4'-dichlorobenzhydryl chloride

Forty-two milliliters of thionyl chloride were gradually added to 75 g of 4,4'-dichlorobenzhydrol. When the addition was complete, the reaction was heated on a steam bath for 2 hours. The excess thionyl chloride was removed in vacuo. One hundred milliliters of carbon tetrachloride were added, and the solvent was again evaporated. The carbon tetrachloride treatment was repeated and upon evaporation the resulting oil was crystallized from peotroleum ether to provide 65.3 g of the desired sub-titled intermediate, m.p. 63° C.

B. Preparation of 2-[bis(4-chlorophenyl)methyl]-2H-tetrazole

A mixture of 3.12 g of tetrazole, 26.2 g of potassium carbonate, and 10 g of 4,4'-dichlorobenzhydryl chloride from above in 150 ml of dimethylformamide was heated under a nitrogen atmosphere for 2.5 hours at 85°–90° C. and then overnight at 60°–65° C. The reaction mixture was poured into 1 liter of a saturated aqueous sodium chloride solution which was then extracted twice with 200 ml portions of ethyl acetate. The combined organic extracts were washed three times with a saturated sodium chloride solution, dried over magnesium sulfate, and evaporated to dryness to provide 12.1 g of the crude product as a pale yellow oil. The residue was purified by high pressure liquid chromatography. The primary product which was recovered was 1.1 g of the 2-tetrazole derivative as white crystals when recrystallized from methanol, m.p. 91°–92° C. Mass spectral analysis confirmed that the product had the correct molecular formula (M+=305) and $^{13}C$ and $^1H$ NMR NOE experiments confirmed that the primary product was 2-[bis(4-chlorophenyl)methyl]-2H-tetrazole.

Analysis for $C_{14}H_{10}Cl_2N_4$: Calculated: C, 55.10; H, 3.30; N, 18.36; Found: C, 55.05; H, 3.45; N, 18.18.

EXAMPLE 2

1-[bis(4-chlorophenyl)methyl]-1H-1,2,3-triazole

Following the general procedure of Example 1B, 5.0 g of 1,2,3-triazole in 100 ml of dimethylformamide were treated first with 1.44 g of sodium hydride (60% in mineral oil), and then with 5.0 g of 4,4'-dichlorobenzhydryl chloride. The reactants were stirred overnight at about 25° C. and then heated for 1 hour on a steam bath. Chromatography of the residue after work-up provided 2.4 g of the undesired 2-[bis(4-chlorophenyl)methyl]-2H-1,2,3-triazole and 3.1 g of the desired title product, m.p. 124°–125° C.

Analysis for $C_{15}H_{11}Cl_2N_3$: Calculated: C, 59.23; H, 3.65; N, 13.81; Found: C, 59.45; H, 3.86; N, 13.81.

The compounds provided by this invention are useful in preventing or therapeutically treating estrogen-dependent diseases, including breast cancer, in mammals by virtue of their ability to inhibit the enzyme aromatase. Their ability to inhibit aromatase was demonstrated by employing a modification of the isolated rat ovarian microsome method of Brodie et al. in *J. Steroid Biochem.*, 7, 787 (1976). In this test system, ovarian microsomes are obtained from rats treated with pregnant mares serum gonadotropin. Test compounds are added to reaction vials containing 0.1 μM 4-androstene-3,17-dione, 100,000 dpm 1,2[$^3$H]-androstenedione, the microsomes and a NADPH generating system. The concentrations of the inhibitors tested ranged between 0.005 and 10 μM. In this assay, aromatization of androstenedione results in the production of [$^3$H]-H$_2$O which is isolated by extracting the samples with chloroform and treating the aqueous phase with charcoal to remove the free steroid. Samples are counted in a liquid scintillation spectrometer and the percent inhibition determined by comparing the results with control samples incubated without inhibitor. Potency is determined based on the concentration of inhibitor in μM required to produce a 50% inhibition of enzyme activity (EC$_{50}$) when the concentration of substrate (androstenedione) is 0.1 μM. The EC$_{50}$'s of certain of the compounds of the above formula are summarized in Table 1.

TABLE 1

| Aromatase Inhibition in the Rat Ovarian Microsome Assay | |
| --- | --- |
| Compound | EC$_{50}$* |
| 1-[bis(4-chlorophenyl)-methyl]-1H—1,2,3-triazole | <0.05 |
| 2-[bis(4-chlorophenyl)-methyl]-2H—tetrazole | 0.15 |

*Concentration of compound in μM required to achieve 50% inhibition of aromatase activity when substrate concentration is 0.1 μM.

The compounds may be administered by any number of routes, including the oral, subcutaneous, intramuscular, intravenous, transdermal, and rectal routes. The compounds are usually employed in the form of pharmaceutical compositions. Such compositions are prepared in a manner well known in the pharmaceutical art and comprise at least one active compound of the above formula.

Accordingly, the invention includes a pharmaceutical composition comprising as active ingredient a compound of the above formula associated with a pharmaceutically acceptable carrier. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, emulsions, solutions, syrups, suspensions, aerosols (as a solid or in a liquid medium), ointments containing for example up to 10% by weight of the active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The formulations can additionally include lubricating agents, wetting agents, emulsifying and suspending agents, preserving agents, sweetening agents or flavoring agents. The compositions of the invention may be formulated so as to provide quick, sustained, or delayed release of the active ingredient after administration to the patient by employing procedures well known in the art.

For oral administration, a compound of this invention can be admixed with carriers and diluents molded into tablets or enclosed is gelatin capsules. The mixtures can alternatively be dissolved in liquids such as ten percent aqueous glucose solution, isotonic saline, sterile water, or the like, and administered intravenously or by injection. Such solutions can, if desired, be lyophilized and stored in a sterile ampoule ready for reconstitution by the addition of sterile water for ready intramuscular injection.

The compositions are preferably formulated in a unit dosage form, each dosage containing from about 1 to about 500 mg, more usually about 5 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The active compounds are effective over a wide dosage range. For example, dosages per day will normally fall within the range of about 0.05 to about 300 mg/kg of body weight. In the treatment of adult humans, the range of about 0.1 to about 50 mg/kg, in single or divided doses, is preferred. However, it will be understood that the amount of the compound actually administered will be determined by a physician, in the light of the relevant circumstances including the condition to be treated, the choice of compound to be administered, the age, weight, and response of the individual patient, the severity of the patient's symptoms, and the chosen route of administration, and therefore the above dosage ranges are not intended to limit the scope of the invention in any way.

In order to more fully illustrate the operation of this invention, the following formulation examples are provided. The examples are illustrative only and are not intended to limit the scope of the invention. The formulations employ as active compounds any of the pharmaceutical compounds of the above formula.

EXAMPLE 3

Hard gelatin capsules are prepared using the following ingredients:

|  | per capsule |
|---|---|
| 1-[bis(4-fluorophenyl)methyl]-1H—1,2,3-triazole | 250 mg |
| Starch dried | 200 mg |
| Magnesium stearate | 10 mg |
| Total | 460 mg |

The above ingredients are mixed and filled into hard gelatin capsules in 460 mg quantities.

EXAMPLE 4

Capsules each containing 20 mg of medicament are made as follows:

|  | per capsule |
|---|---|
| 1(2)-[(4-chlorophenyl)(4-fluorophenyl)methyl]-1H(2H)—tetrazole | 20 mg |
| Starch | 89 mg |
| Microcrystalline cellulose | 89 mg |
| Magnesium stearate | 2 mg |
| Total | 200 mg |

The active ingredient, cellulose, starch and magnesium stearate are blended, passed through a No. 45 mesh U.S. sieve and filled into hard gelatin capsules in 200 mg quantities.

EXAMPLE 5

Capsules each containing 100 mg of active ingredient are made as follows:

|  | per capsule |
|---|---|
| 1-[(4-trifluoromethylphenyl)(3-pyridyl)methyl]-1H—1,2,3-triazole | 100 mg |
| Polyoxyethylenesorbitan monooleate | 50 mcg |
| Starch powder | 250 mg |

The above ingredients are thoroughly mixed and are placed in an empty gelatin capsule.

EXAMPLE 6

Tablets each containing 10 mg of active ingredient are made up as follows:

|  | per tablet |
|---|---|
| 1(2)-[(2,4-dichlorophenyl)(4-chlorophenyl)methyl]-1H(2H)—tetrazole | 10 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 100 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 100 mg.

EXAMPLE 7

A tablet formula is prepared using the ingredients below:

|  | per tablet |
|---|---|
| 1-[1-(4-chlorophenyl)-1-phenyl-ethyl]-1H—1,2,3-triazole | 250 mg |
| Cellulose microcrystalline | 400 mg |
| Silicon dioxide fumed | 10 mg |
| Stearic acid | 5 mg |
| Total | 665 mg |

The components are blended and compressed to form tablets each weighing 665 mg.

EXAMPLE 8

Suppositories each containing 25 mg of active ingredient are made as follows:

|  | per suppository |
|---|---|
| 1-[(4-methylphenyl)(4-methoxyphenyl)methyl]-1H—1,2,3-triazole | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

EXAMPLE 9

Suspensions each containing 5 mg of medicament per 5 ml dose are made as follows:

|  | per 5 ml of suspension |
|---|---|
| 1(2)-[(3-pyridyl)(3,4-difluorophenyl)methyl]-1H(2H)—tetrazole | 5 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxyethylcellulose and syrup to form a smooth paste. The benzoic acid solution, flavor and color is diluted with some of the water and added, with stirring. Sufficient water is then added to produce the required volume.

EXAMPLE 10

An aerosol solution is prepared containing the following components:

|  | Weight % |
|---|---|
| 1-(diphenylmethyl)-1H—1,2,3-triazole | 0.25 |
| Ethanol | 29.75 |
| Propellant 22 (Chlorodifluoromethane) | 70.00 |

The active compound is mixed with ethanol and the mixture added to a portion of the propellant 22, cooled to −30° C. and transferred to a filling device. The required amount is then fed to a stainless steel container and diluted further with the remaining amount of propellant. The valve units are then fitted to the container.

We claim:

1. A method of inhibiting aromatase in a mammal which comprises administering to said mammal an aromatase inhibiting amount of a compound of the formula $$\begin{array}{c}\text{N} \\ \text{N} \\ \text{E}=\text{Q}\end{array}\text{N}-\overset{H}{\underset{R}{C}}-\underset{R_2}{\overset{R_1}{\bigcirc}}$$

wherein R is pyridyl or $$\underset{6'\quad 5'}{\overset{2'\quad 3'}{\bigcirc}}\begin{array}{c}R_3 \\ R_4\end{array}$$

$R_1$, $R_2$, $R_3$, and $R_4$ are independently hydrogen, methyl, trifluoromethyl, methoxy, or halo; and E and Q are independently N or CH, with the proviso that E and Q may not both be N at the same time, or a pharmaceutically acceptable salt thereof.

2. The method of claim 1 employing a compound wherein R is $$\bigcirc\begin{array}{c}R_3. \\ R_4\end{array}$$

3. The method according to claim 2 employing a compound wherein $R_1$ and $R_3$ are independently chloro or fluoro.

4. The method according to claim 3 employing 1-[bis(4-chlorophenyl)methyl]-1H-1,2,3-triazole or a pharmaceutically acceptable salt thereof.

5. The method according to claim 3 employing 2-[bis(4-chlorophenyl)methyl]-2H-tetrazole or a pharmaceutically acceptable salt thereof.

6. A method of preventing or treating estrogen-dependent diseases in a mammal which comprises administering to said mammal an effective amount of a compound of the formula

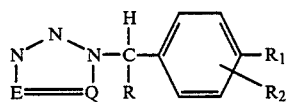

wherein R is pyridyl or

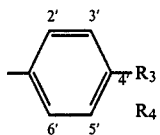

$R_1$, $R_2$, $R_3$, and $R_4$ are independently hydrogen, methyl, trifluoromethyl, methoxy, or halo; and E and Q are independently N or CH, with the proviso that E and Q may not both be N at the same time, or a pharmaceutically acceptable salt thereof.

7. The method according to claim 6 employing 1-[bis(4-chlorophenyl)methyl]-1H-1,2,3-triazole or a pharmaceutically acceptable salt thereof.

8. The method according to claim 6 employing 2-[bis(4-chlorophenyl)methyl]-2H-tetrazole or a pharmaceutically acceptable salt thereof.

9. The method according to claim 6 wherein the estrogen-dependent disease is breast cancer.

10. The method according to claim 9 employing 1-[bis(4-chlorophenyl)methyl]-1H-1,2,3-triazole or a pharmaceutically acceptable salt thereof.

11. The method according to claim 9 employing 2-[bis(4-chlorophenyl)methyl]-2H-tetrazole or a pharmaceutically acceptable salt thereof.

12. A pharmaceutical formulation which comprises a compound of the formula

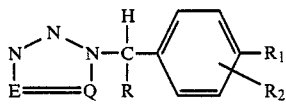

wherein R is pyridyl or

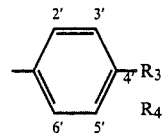

$R_1$, $R_2$, $R_3$, and $R_4$ are independently hydrogen, methyl, trifluoromethyl, methoxy, or halo; and E and Q are independently N or CH, with the proviso that E and Q may not both be N at the same time, or a pharmaceutically acceptable salt thereof, in combination with a suitable pharmaceutical carrier, diluent, or excipient therefor.

13. A formulation according to claim 12 employing a compound wherein R is

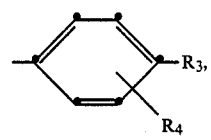

$R_1$ and $R_3$ are independently chloro or fluoro, and $R_2$ and $R_4$ are each hydrogen.

14. A formulation according to claim 13 employing 1-[bis(4-chlorophenyl)methyl]-1H-1,2,3-triazole or a pharmaceutically acceptable salt thereof.

15. A formulation according to claim 13 employing 2-[bis(4-chlorophenyl)methyl]-2H-tetrazole or a pharmaceutically acceptable salt thereof.

* * * * *